US00PP19234P2

(12) United States Plant Patent
Lamb et al.

(10) Patent No.: US PP19,234 P2
(45) Date of Patent: Sep. 16, 2008

(54) ***ANTHURIUM* PLANT NAMED 'TWYANBP5'**

(50) Latin Name: ***Anthurium* hybrid**
Varietal Denomination: TWYANBP5

(75) Inventors: Ann E. Lamb, Sebring, FL (US); Marianne E. Knauss, Longwood, FL (US)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/973,533

(22) Filed: Oct. 9, 2007

(51) Int. Cl.
*A01H 5/00* (2006.01)

(52) U.S. Cl. ..... Plt./367
(58) Field of Classification Search ..... Plt./367
See application file for complete search history.

*Primary Examiner*—Annette H Para
(74) *Attorney, Agent, or Firm*—Jondle & Associates, P.C.

(57) ABSTRACT

A new *Anthurium* plant particularly distinguished by having numerous, large for type, glossy, medium-pink spathes, durable, shiny leaves and is easy to grow, is disclosed.

1 Drawing Sheet

Genus and species: *Anthurium* hybrid.
Variety denomination: 'TWYANBP5'

BACKGROUND OF THE NEW PLANT

The present invention comprises a new and distinct cultivar of *Anthurium,* botanically known as *Anthurium* hybrid, and hereinafter referred to by the cultivar name 'TWYANBP5'. The new cultivar originated from a hybridization made in March of 2004 in Apopka, Fla., USA. The female parent was the proprietary *Anthurium* plant 'Ruby Gem' (unpatented), while the male parent was the *Anthurium* plant 'Gemini' (U.S. Plant Pat. No. 10,043).

The new cultivar was selected in May of 2006 from the results of the hybridization and has been asexually reproduced repeatedly by tissue culture in Apopka, Fla., USA. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1) Numerous, large for type, glossy, medium-pink spathes;
2) Durable, shiny leaves; and
3) Easy to grow.

DESCRIPTION OF PHOTOGRAPH

This new *Anthurium* plant is illustrated by the accompanying photograph which shows the overall plant habit including blooms, buds and foliage of the plant. The colors shown are as true as can be reasonably obtained by conventional photographic procedures. The photograph is of an 18-month old plant grown in a greenhouse in Apopka, Fla.

DESCRIPTION OF THE NEW CULTIVAR

The following detailed description sets forth the distinctive characteristics of 'TWYANBP5'. The data which define these characteristics were collected from asexual reproductions carried out in Apopka, Fla. The plant history was taken on 18-month old plants which were planted from tissue culture in 25-cm pots and grown in a greenhouse with average daily temperatures of 85° C.–95° F. and average nightly temperatures of 72° C. to 78° F. Observations were made in March 2007. Color readings were taken under natural light in the greenhouse. Color references are primarily to the RHS Colour Chart of The Royal Horticultural Society of London (RHS) (2001).

DETAILED BOTANICAL DESCRIPTION

Classification:
- *Family.*—Aracea.
- *Botanical.*—*Anthurium* hybrid.
- *Common.*—*Anthurium.*

Parentage:
- *Female parent.*—*Anthurium* plant 'Ruby Gem' (unpatented) with dark red-pink spathes.
- *Male parent.*—*Anthurium* plant 'Gemini' (U.S. Plant No. 10,043) with red-pink spathes.

Growth:
- *Form.*—Upright, symmetrical, with outward arching leaves.
- *Growth and branching habit.*—Upright stems, branched habit (basal, axillary branching), with many leaves and flowers; vigorous growth habit, plant produces numerous branches, leaves and flowers.
- *Height* (*measured from soil to top of canopy*).—46 cm.
- *Height* (*measured from soil to top of inflorescences*).—55 cm (flowers at, among and above the top of the foliage).
- *Width* (*area of spread*).—63 cm.
- *Time to produce a finished flowering plant.*—Single micro cutting to linear: 14 to 16 weeks. 10 cm pot from liner: 6 to 7 months (first flowers). 15 cm pot from liner: 9 to 10 months. 20 cm pot from liner: 12 to 14 months.
- *Growth rate.*—Typical of commercial *Anthurium* cultivars.

*Root description.*—Thick fleshy roots with finer laterals; RHS 155C to RHS 195B (greenish-white); RHS 181B to RHS 45B where exposed to light; RHS 151D root tips.

*Durability of foliage to stresses.*—Durable, holds up well under typical commercial practice.

*High temperature tolerance.*—To about 104° F. without damage.

*Lower temperature tolerance.*—To about 55° F. without damage.

Stems:

*Number of stems per plant.*—10.

*Length (from soil line to the junction of the last two unrolled leaves).*—12 cm.

*Diameter (measured from about 5 cm above the soil surface).*—1.4 cm.

*Internode length.*—1.5 cm.

*Color.*—Immature: RHS 145A sheathed with green cataphylls. Mature: RHS 146B to RHS 146C sheathed with RHS N199B and RHS 165A dried brown cataphylls.

*Appearance (shape).*—Upright, cylindrical, round, thick with regularly spaced petioles and short internodes; catalyphylls are present and non-persistent; surface texture is smooth and glossy.

*Aspect.*—Upright.

*Strength.*—Sturdy, tough, upright.

*Cataphylls.*—Shape and arrangement: Lanceolate, acute to obtuse, mucronate, one or two keeled; base of cataphyll claps the stem. Length: 4.0 cm to 11.0 cm. Width: 3.4 cm (flattened). Texture: Inside: Shiny, smooth. Outside: Glossy. Color: RHS 145A to RHS 145B, distal keel often tinged with RHS 51C when new, becoming RHS N199B to RHS 165A with senescence.

Leaves:

*Arrangement and type.*—Alternate, simple, single leaf per petiole, midrib on lower surface is keeled.

*Quantity of leaves per stem.*—8 per main stem; fewer leaves on younger axillary branches.

*Length.*—19 cm to 23 cm.

*Width (natural).*—12 cm to 16 cm.

*Width (flattened).*—13 cm to 17.5 cm.

*Shape.*—Ovate to somewhat deltoid; leaf blade folded upward lengthwise.

*Apex.*—Acute to acuminate, mucronate.

*Base.*—Truncate to slightly cordate.

*Margin.*—Entire, with some undulations; leaf blade folded upward lengthwise.

*Texture.*—Smooth, medium thickness, rigid, firm/leathery, very shiny, dulling with age.

*Pubescence.*—None.

*Immature leaves color.*—Upper surface: RHS 147B to RHS 146B to RHS 146C. Lower surface: RHS 147B to RHS 147C.

*Mature leaves color.*—Upper surface: RHS 147A to RHS N189A. Lower surface: RHS 147B to RHS 146B.

*Venation.*—Pinnate, radiating outward from the midrib in a herringbone arrangement. Venation color: Upper surface: Immature: RHS 146B. Immature midrib: RHS 144A to RHS 146B. Mature: RHS 147B often tinged with RHS 183A. Mature midrib: RHS 146A often tinged with RHS 183D. Lower surface: Immature: RSH 144B to RHS 144C. Immature midrib: RHS 144B to RHS 144C. Mature: RHS 147B to RHS 146B. Mature midrib: RHS 145A tinged with RHS 183D.

*Petiole.*—Aspect: Vertical and upright when newly emerged, becoming about 45° from the vertical axis with maturity. Length (from base of leaf to junction of petiole and stem): 25 cm to 34 cm. Diameter: Distal (measured in the center below the geniculum and above the petiole wing tip): 0.40 cm. Proximal: 0.11 cm. Color: RHS 146A to RHS 146B faintly tinged with RHS 183D.

*Geniculum.*—Length: 4.9 cm to 6.5 cm. Diameter: 0.5 cm. Aspect: Straight or curved outward. Color: RHS 146A to RHS 146B.

*Wing.*—Length: 4.0 cm (tip of wing bluntly rounded). Diameter: 0.6 cm. Color: Outside: RHS 145A to RHS 146D. Inside: RHS 145B to RHS 145C.

Inflorescence:

*Arrangement.*—Spathe/spadix atop peduncle, emerges from petiole sheath; peduncle attached to stem at leaf axil; inflorescences loosely grouped along the center of the plant; persistent.

*Aspect.*—Upright straight, vertical when newly emerged, leaning outward up to about 45° with age.

*Height.*—55 cm.

*Depth.*—Spathe nearly flat, or cupped upward 1.5 cm deep.

*Flowering habit and season.*—Continuous flowering year round, but most prolific in winter and spring.

*Number of inflorescences per plant.*—26 inflorescences and buds.

*Fragrance.*—Absent.

*Rate of inflorescence opening.*—About every 14 days 2 to 3 new inflorescence emerge.

*Longevity on plant.*—6 to 8 weeks.

*Longevity as cut flower.*—14 days.

Spathe:

*Appearance.*—Relatively large for type, red-pink, margins slightly cupped upward.

*Arrangement/Aspect.*—Variable, typically horizontal or about 45° from the vertical axis.

*Texture.*—Glossy, medium thickness, firm/leathery, slightly concave between veins.

*Shape.*—Broadly ovate.

*Margin.*—Entire, often slightly recurved.

*Apex.*—Acute to somewhat acuminate, mucronate.

*Base.*—Slightly cordate.

*Longevity.*—6 to 8 weeks with good color.

*Size.*—Length: 9.5 cm to 12 cm. Width (natural): 7.0 cm to 7.9 cm. Width (flattened): 7.5 cm to 8.1 cm.

*Color.*—When opening: Front side: RHS 47A to RHS 47B. Rear side: RHS 46D. Fully opened: Front side: RHS 47B to RHS 45D. Rear side: RHS 47A to RHS 45D. Fading to: RHS 180A and RHS 178B tinged with RHS 146C (green).

Spadix:

*Appearance.*—Columnar, upright, affixed atop very short stipe at junction of peduncle and spathe.

*Arrangement/Aspect.*—Upright, near vertical, or tilted outward.

*Shape.*—Columnar, narrower, tapered at tip; apex bluntly rounded.

*Margin.*—Round in transverse section.

*Apex.*—Bluntly rounded, obtuse.

*Base.*—Bluntly rounded, terminates atop a short stipe.

*Size.*—Length: 4.9 cm to 7.9 cm. Diameter: 0.8 cm to 0.95 cm.

*Color* (*immature*).—Overall: RHS 8D overall. Apex: RHS 5C.

*Color* (*mature*).—RHS 155A; variable with maturity, becoming RHS 174B variably tinged with RHS 182A and/or RHS 146C; may fade entirely to RHS 146C (green).

Flowers:

*Arrangement.*—Flowers reduced, tightly packed on spadix.

*Type.*—Bisexual, reduced, minuscule; female flowers receptive first, followed by male flowers.

*Shape.*—Individual flowers roughly pyramidal in shape, tightly packed on the spadix; flowers nearly sessile on spadix; face of individual flower flat and square or diamond shaped; pistil in center, protruding, surrounded by anthers; four triangular tepals at corners.

*Diameter.*—0.20 cm.

*Height.*—0.3 cm from base to tip of pistil; stigma protrudes about 0.01 cm when receptive.

*Number of female flowers are spadix.*—220.

*Number of male anthers per flower.*—About 8 (minuscule; not clearly visible).

Peduncle:

*Length.*—38 cm.

*Diameter.*—0.40 cm.

*Angle.*—Straight, upright or curved outward.

*Strength.*—Sturdy, somewhat flexible.

*Color.*—RHS 146B to RHS 146C faintly tinged distally with RHS 183A.

Pedicel:

*Length.*—Stipe reduced, flower nearly sessile.

*Diameter.*—Stipe 0.35.

*Angle.*—Straight, upright or leaning outward slightly.

*Strength.*—Sturdy.

*Color.*—RHS 47D.

Reproductive organs:

*Anther color.*—RHS 8D to RHS 155A.

*Pollen amount.*—Sparse.

*Pollen color.*—RHS 155D (white).

*Stigma color.*—RHS 155A (white).

*Ovary color.*—Pale RHS 155A.

Fruit and seed set: Seed production has not been observed to date

Disease and insect resistance: No particular resistance or susceptibility different from other *Anthurium* varieties.

COMPARISON WITH PARENTAL AND COMMERCIAL CULTIVARS

'TWYANBP5' differs from the female parent *Anthurium* plant 'Ruby Gem' (unpatented), by having larger, wider, medium-pink spathes and a pale-yellow spadix, while 'Ruby Gem' has smaller, narrower, dark red-pink spathes and a purple spadix. 'TWYANBP5' has a larger, more upright and faster growth habit, while 'Ruby Gem' has a shorter, more spreading and slower growth habit. In addition, 'TWYANBP5' has larger, shiny leaves, while 'Ruby Gem' has smaller leaves with less gloss.

'TWYANBP5' differs from the male parent Anthurium plant 'Gemini' (U.S. Plant Pat. No. 10,043) by having larger, medium-pink spathes, while 'Gemini' has smaller, darker, red-pink spathes. 'TWYANBP5' has leaves that are larger, thicker and shinier, while 'Gemini' has leaves that are smaller, less rigid and have less gloss. In addition, 'TYWANBP5' is a larger overall plant, while 'Gemini' is a smaller plant.

'TWYANBP5' differs from the commercial variety 'Misty Rose' (U.S. Plant Pat. No. 14,475), by having larger spathes and a pale-yellow spadix, while 'Misty Rose' has smaller spathes with a pink spadix. 'TWYANBP5' has leaves that are ovate to deltoid, thicker and shiny, while 'Misty Rose' has leaves that are more triangular, less rigid and have less gloss. In addition, 'TWYANBP5' has a more prolific bloom that 'Misty Rose'.

I claim:

1. A new and distinct cultivar of *anthurium* plant as shown and described herein.

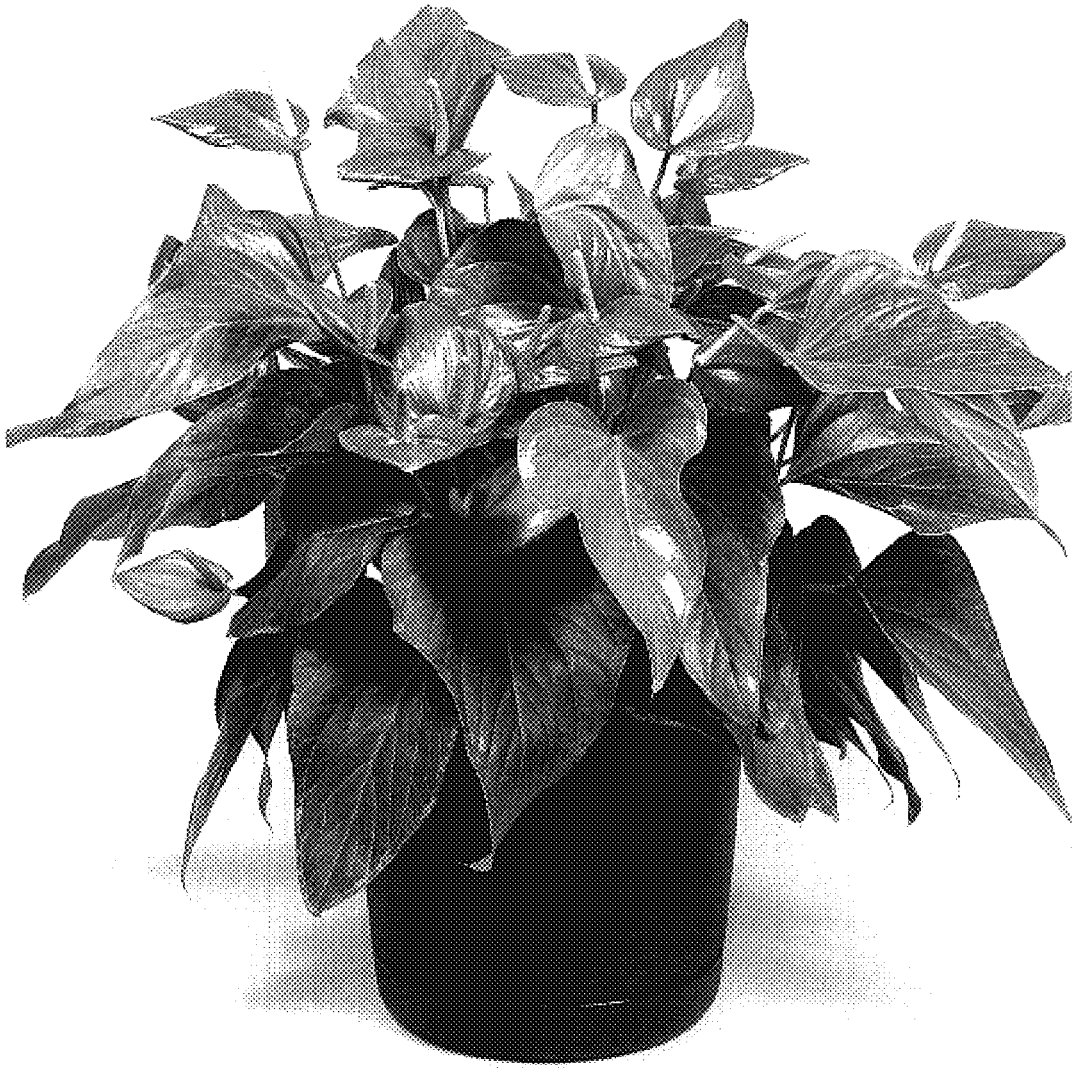

* * * * *